(12) United States Patent
McCarty

(10) Patent No.: US 6,329,361 B1
(45) Date of Patent: *Dec. 11, 2001

(54) HIGH-DOSE CHROMIC PICOLINATE TREATMENT OF TYPE II DIABETES

(75) Inventor: Mark F. McCarty, San Diego, CA (US)

(73) Assignee: Nutrition 21, San Deigo, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/440,362

(22) Filed: May 12, 1995

(51) Int. Cl.$^7$ .......................... A61K 31/555; A61K 31/28
(52) U.S. Cl. .......................... 514/188; 514/505; 514/866
(58) Field of Search .................................... 514/188, 866, 514/505

(56) References Cited

U.S. PATENT DOCUMENTS

| | | | |
|---|---|---|---|
| 4,315,927 | * 2/1982 | Evans | 424/254 |
| 5,087,623 | * 2/1992 | Boynton et al. | 514/188 |
| 5,164,384 | 11/1992 | Paul | 514/188 |

OTHER PUBLICATIONS

R.A. Anderson (1986) Chromium metabolism and its role in disease processes in man. Clin. Physiol. Biochem. 4:31–41.

E. Boyle, Jr. et al. (1977) Chromium depletion in the pathogenesis of diabetes and atherosclerosis. Southern Med. Jour. 70(12):1449–1453.

N.A. Lee et al. (1994) Beneficial effect of chromium supplementation on serum triglyceride levels in NIDDM. Diabetes Care. 17(12):1449–1452.

Nat. Acad. of Sciences (1980) Recommended dietary allowances. Ninth Revised Ed. 159–161.

F. Xavier Pi—Sunyer et al. (1984) Present knowledge in nutrition. Nutrition Reviews' Fifth Ed. 570–587.

McCarty, M. F. (1991) The case for supplemental chronium and survey of clinical with chromium picolinate. Journal of Applied Nutrition. 431:58–66.

McCarty, M.F. (1993) Homologous physiological effects of phenformin and Chronium picolinate. Medical Hypothesis. 41:316–324.

\* cited by examiner

*Primary Examiner*—Jerome D. Goldberg
(74) *Attorney, Agent, or Firm*—Knobbe, Martens, Olson & Bear, LLP

(57) ABSTRACT

A method for stabilizing blood glucose levels and reducing the hyperglycemia associated with Type II diabetes. Synthetic chromic tripicolinate is administered either orally or parenterally to a human in need thereof at a dosage of between about 1,000 amd 10,000 micrograms per day.

5 Claims, No Drawings

HIGH-DOSE CHROMIC PICOLINATE TREATMENT OF TYPE II DIABETES

FIELD OF THE INVENTION

The present invention relates to the treatment of adult-onset non-insulin dependent diabetes mellitus (NIDDM). More specifically, the invention relates to the treatment of this form of diabetes by administering high doses of chromium in the form of chromic picolinate.

BACKGROUND

Diabetes is known to affect at least 10 million Americans, and millions more may unknowingly have the disease. In the form of this disease known as Type II, non-insulin dependent, or adult-onset (as opposed to juvenile diabetes), the pancreas often continues to secrete normal amounts of insulin. However, this insulin is ineffective in preventing the symptoms of diabetes which include hyperglycemia, impaired carbohydrate metabolism, glycosuria and decreased insulin sensitivity. These symptoms, if left untreated, often lead to severe complications.

Chromium is a nutritionally essential trace element. The essentiality of chromium in the diet was established in 1959 by Schwartz, as cited in *Present Knowledge in Nutrition*, page 571, fifth edition (1984, The Nutrition Foundation, Washington, D.C.). Chromium depletion is characterized by the disturbance of glucose, lipid and protein metabolism and by a shortened lifespan. Chromium is essential for optimal insulin activity in all known insulin-dependent systems (Boyle et al., *Southern Med. J.*, 70:1449–1453, 1977). Insufficient dietary chromium has been linked to both maturity-onset diabetes and to cardiovascular diseases.

The principle energy sources for the body are glucose and fatty acids. Chromium depletion results in biologically ineffective insulin and compromised glucose metabolism. Under these conditions, the body must rely primarily on lipid metabolism to meet its energy requirements, resulting in the production of excessive amounts of acetyl-CoA and ketone bodies. Some of the accumulated acetyl-CoA is diverted to increased cholesterol biosynthesis, resulting in hypercholesterolemia. Diabetes mellitus is characterized in large part by glycosuria, hypercholesterolemia, and often ketoacidosis. The accelerated atherosclerotic process seen in diabetics is associated with hypercholesterolemia (Boyle et al., Supra).

Current drugs used for managing Type II diabetes fall within two classes of compounds: the biguanides and the sulfonylureas. The biguanides, e.g. Metformin, have been approved for use in the U.S. due to induction of lactic acidosis. The sulfonylureas, e.g. tolbutamide and glyburide, lower plasma glucose primarily by stimulating insulin secretion and by enhancing insulin effects in some target tissues and by inhibiting hepatic glucose synthesis.

Supplementation of chromium to normal individuals has been reported to lead to improvements in glucose tolerance, serum lipid concentrations, including high-density lipoprotein cholesterol, insulin and insulin binding (Anderson, *Clin. Physiol. Biochem.*, 4:31–41, 1986). Supplemental chromium in the trivalent form, e.g. chromic chloride, is associated with improvements of risk factors associated with adult-onset diabetes and cardiovascular disease.

Chromium is known to function as a co-factor for the action of insulin. It binds to insulin and potentiates many, and perhaps all, of its functions (Boyle et al., supra). These functions include, but are not limited to, the regulation of carbohydrate and lipid metabolism (*Present Knowledge in Nutrition*, supra, at p. 573–577).

The introduction of organic chromium compounds per se into individuals is not particularly beneficial. Chromium must be converted endogenously into an organic complex or must be consumed as a biologically active molecule. Only about 0.5% of ingested organic chromium is assimilated into the body (*Recommended Daily Allowances*, Ninth Revised Edition, The National Academy of Sciences, page 160, 1980). Only 1–2% of most chromium compounds is assimilated into the body.

U.S. Pat. No. 4,315,927 describes the discovery that when selected essential metals are administered to mammals as exogenously synthesized coordination complexes of picolinic acid, they are directly available for absorption into the system without competition from other metals. This patent describes a composition and method for selectively supplementing the essential metals in the human diet and for facilitating absorption of these metals by intestinal cells. These complexes are safe, inexpensive, biocompatible and easy to produce. These exogenously synthesized essential metal coordination complexes of picolinic acid (pyridine-2-carboxylic acid) have the following structural formula:

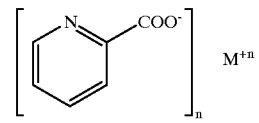

wherein M represents the metallic cation and n is equal to the cation's valence. For example, when M is Cr and n=3, then the compound is chromic tripicolinate. Other chromium picolinates could include $M=Cr^{+3}$ and n=2 (chromic dipicolinate) or n=1 (chromium monopicolinate).

The U.S. Recommended Daily Allowance (RDA) for chromium is 50–200 micrograms. U.S. Pat. No. 5,087,623 describes the administration of chromic tripicolinate for the treatment of adult-onset diabetes in doses ranging from 50 to 500 micrograms.

Thus, there is a need for a safe, effective, inexpensive composition capable of significantly lowering blood sugar levels to an acceptable value. The present invention satisfies this need.

SUMMARY OF THE INVENTION

We have unexpectedly discovered that chromic tripicolinate administered at doses an order of magnitude higher than the RDA can dramatically lower blood glucose levels in individuals having adult-onset diabetes.

The present invention provides a method for reducing hyperglycemia and stabilizing the level of serum glucose in humans comprising administering between about 1,000 and 10,000 micrograms per day of chromium as synthetic chromic tripicolinate to a human in need thereof. Preferably, the amount of chromium administered is between about 1,000 and 5,000 micrograms per day of chromium as synthetic chromic tripicolinate. The chromic tripicolinate is advantageously provided in a pharmaceutically acceptable carrier. According to one aspect of this preferred embodiment, the chromic tripicolinate is orally administered. Alternatively, the chromic tripicolinate is parenterally administered.

DETAILED DESCRIPTION OF THE INVENTION

The present invention relates to the discovery that doses of chromium, administered in the form of chromic tripicolinate, about an order of magnitude higher than the U.S. RDA, promote a significant reduction in blood glucose levels in individuals with Type II diabetes. This reduction is markedly greater than that seen after administration of chromium doses falling within the RDA of chromium and indicates that high doses of chromium picolinate are effective in stabilizing blood glucose levels.

Because chromium is a cofactor which potentiates the action of insulin, it would be expected that an individual receiving a dosage of chromium at the upper end of the RDA range would bind all available insulin, resulting in a maximal reduction in blood glucose levels. In view of this, administration of chromium doses significantly higher than the RDA would not be expected to exert a blood glucose-lowering effect beyond that seen at the upper end of the RDA range, due to saturation of the chromium binding sites on all of the available insulin. Unexpectedly, a daily dose of 1,000 micrograms of chromium administered as chromium tripicolinate, five times higher than the upper limit of the proposed recommended daily intake (120 $\mu$g per day for chromium) significantly reduced blood glucose levels as assessed by a reduction in glycosylated hemoglobin. The therapeutic benefit of chromium tripicolinate is thus clearly dose-dependent, and dosages falling within the so-called "nutritional range" are unlikely to be of significant therapeutic benefit in the treatment of Type II diabetes.

The synthesis of chromic picolinates is described in U.S. Pat. No. 5,087,623, the entire contents of which are hereby incorporated by reference. In order to reduce the requirement for insulin and/or diabetic drugs and to reduce several important risk factors associated with Type II diabetes, it is anticipated that the dosage range of chromium administered to a patient in the form of chromic tripicolinate will be between about 1,000 and 10,000 micrograms per day. In a preferred embodiment, this amount is between about 1,000 and 5,000 micrograms per day.

Although the administration of chromic tripicolinate for treatment of Type II diabetes is described herein, the administration of chromic monopicolinate and chromic dipicolinate to a patient in need thereof is also within the scope of the invention.

For oral administration, the chromic picolinates may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and such compositions may contain one or more of the following agents: sweeteners, flavoring agents, coloring agents and preservatives. The sweetening and flavoring agents will increase the palatability of the preparation. Tablets containing chromic tripicolinate in admixture with non-toxic pharmaceutically acceptable excipients suitable for tablet manufacture are acceptable. Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the chromic tripicolinate complex of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose. Such formulations may also contain a demulcent, a preservative, a flavoring or a coloring agent.

The chromic tripicolinate preparations for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono or diglycerides. In addition, fatty acids such as oleic acid may likewise be used in the preparation of injectable preparations.

The pharmaceutical compositions may also be in the form of oil-in-water emulsions. The oily phase may be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

The amount of chromic tripicolinate that may be combined with the carrier material to produce a single dosage form will vary depending upon the host treated and the particular mode of administration.

A clinical trial of the effect of high doses of chromic tripicolinate on Type II diabetes is described in the following example.

EXAMPLE 1

A High-Dose Chromic Tripicolinate Treatment

A randomized double-blind clinical trial of 180 subjects having Type II diabetes was conducted. One third of the subjects received an oral daily dose of 1,000 micrograms of chromium in the form of chromium picolinate (two 500 microgram capsules); one third received 200 micrograms of chromium; and one third received a placebo. These dosages were administered for four months. At the beginning of the study and after two and four months, fasting and postprandial glucose levels were measured two hours after performance of a glucose tolerance test. Glycosylated hemoglobin levels were also measured by standard methods. The subjects receiving the 1,000 microgram dose of chromium as chromic tripicolinate exhibited an average reduction in glycosylated hemoglobin of 30% and a similar reduction in fasting and postprandial glucose levels (28% and 27%, respectively). A 30% decrease in glycosylated hemoglobin in a diabetic individual corresponds to glycosylated hemoglobin values between about 6 and 8 which are below the 9–12 range observed in most diabetics.

The above description of the invention is set forth solely to assist in understanding the invention. It is to be understood that variations of the invention, including all equivalents now known or later developed, are to be considered as falling within the scope of the invention, which is limited only by the hereafter amended claims.

What is claimed is:

1. A method for reducing hyperglycemia and stabilizing the level of serum glucose in humans comprising the step of administering a composition consisting essentially of between about 1,000 and 10,000 micrograms per day of chromium as synthetic chromic tripicolinate to a human in need of reducing hypergycemis or stabilizing the level of serum glucose.

2. The method of claim 1, comprising administering between about 1,000 and 5,000 micrograms per day of chromium as synthetic chromic tripicolinate.

3. The method of claim 1, wherein said chromic tripicolinate is in a pharmaceutically acceptable carrier.

4. The method of claim 3, wherein said chromic tripicolinate is orally administered.

5. The method of claim 3, wherein said chromic tripicolinate is parenterally administered.

\* \* \* \* \*

UNITED STATES PATENT AND TRADEMARK OFFICE
CERTIFICATE OF CORRECTION

PATENT NO. : 6,329,361 B1
DATED : December 11, 2001
INVENTOR(S) : McCarty

It is certified that error appears in the above-identified patent and that said Letters Patent is hereby corrected as shown below:

<u>Column 6,</u>
Line 12, cancel "hypergycemis" and replace it with -- hyperglycemia --.

Signed and Sealed this

Thirtieth Day of April, 2002

Attest:

Attesting Officer

JAMES E. ROGAN
*Director of the United States Patent and Trademark Office*